(12) United States Patent | (10) Patent No.: US 12,611,168 B2
True et al. | (45) Date of Patent: Apr. 28, 2026

(54) DEVICES, SYSTEMS, AND METHODS FOR POSITIONING MEDICAL DEVICES WITHIN A BODY LUMEN

(71) Applicant: BOSTON SCIENTIFIC SCIMED, INC., Maple Grove, MN (US)

(72) Inventors: Kyle True, Minneapolis, MN (US); Daniel J. Foster, Lino Lakes, MN (US); Dana Sachs, Pine City, MN (US); Alice Herzberg, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/714,850

(22) Filed: Apr. 6, 2022

(65) Prior Publication Data

US 2022/0313208 A1 Oct. 6, 2022

Related U.S. Application Data

(60) Provisional application No. 63/171,198, filed on Apr. 6, 2021.

(51) Int. Cl.
A61B 8/00 (2006.01)
A61B 8/08 (2006.01)
A61B 8/12 (2006.01)

(52) U.S. Cl.
CPC .............. A61B 8/12 (2013.01); A61B 8/4254 (2013.01); A61B 8/4416 (2013.01); A61B 8/4488 (2013.01); A61B 8/5207 (2013.01)

(58) Field of Classification Search
CPC ................................ A61B 8/4254; A61B 8/12
See application file for complete search history.

(56) References Cited

U.S. PATENT DOCUMENTS

| 5,456,258 A | 10/1995 | Kondo et al. |
| 6,224,555 B1 | 5/2001 | Ouchi et al. |
| | (Continued) | |

FOREIGN PATENT DOCUMENTS

| JP | H11347037 A | 12/1999 |
| JP | 2005529701 A | 10/2005 |
| JP | 2012192022 A | 10/2012 |

OTHER PUBLICATIONS

International Search Report and Written Opinion dated Jul. 11, 2022 for International Application No. PCT/US2022/023721.

*Primary Examiner* — Amal Aly Farag
(74) *Attorney, Agent, or Firm* — Seager, Tufte & Wickhem, LLP

(57) ABSTRACT

The present disclosure includes elongate members for positioning medical devices at a target site within a body lumen. In various embodiments, the elongate member may include one or more articulation joints for maneuvering, one or more transducers for localizing, and one or more lumens for delivering instruments to the target site. Some embodiments are particularly directed to a medical device that guides an operator to a target site, confirms the location of the target site, and enables a biopsy to be taken from and/or a therapy to be delivered to the target site. For example, a position tracking sensor may be utilized to guide the medical device to the target site, a phased array sensor may be utilized to confirming proper positioning at the target site, and a biopsy needle inserted through a lumen may be utilized to acquire a sample from the target site.

13 Claims, 11 Drawing Sheets

(56)        References Cited

U.S. PATENT DOCUMENTS

| | | | |
|---|---|---|---|
| 6,302,875 B1 * | 10/2001 | Makower | A61B 17/3439 |
| | | | 604/528 |
| 2004/0082883 A1 | 4/2004 | Kohno et al. | |
| 2008/0194939 A1 * | 8/2008 | Dickinson | A61B 17/2202 |
| | | | 600/407 |
| 2009/0118725 A1 | 5/2009 | Auth et al. | |
| 2014/0005521 A1 * | 1/2014 | Kohler | A61B 6/4057 |
| | | | 601/3 |
| 2014/0276051 A1 * | 9/2014 | Hoffman | A61B 17/3417 |
| | | | 604/164.09 |
| 2016/0287223 A1 * | 10/2016 | Hingston | A61B 8/12 |
| 2017/0265718 A1 * | 9/2017 | Hiraoka | G02B 23/2476 |
| 2018/0168482 A1 * | 6/2018 | Hein | A61M 25/104 |
| 2019/0254649 A1 * | 8/2019 | Walters | A61B 1/07 |
| 2021/0129357 A1 * | 5/2021 | Davison | A61B 17/320092 |

* cited by examiner

100

ELONGATE MEMBER
102

DEVICES, SYSTEMS, AND METHODS FOR POSITIONING MEDICAL DEVICES WITHIN A BODY LUMEN

CROSS REFERENCE TO RELATED APPLICATIONS

The present application claims the benefit of and priority to U.S. Provisional Patent Application No. 63/171,198, filed Apr. 6, 2021 and titled DEVICES, SYSTEMS, AND METHODS FOR POSITIONING MEDICAL DEVICES WITHIN A BODY LUMEN, the disclosure of which is incorporated herein by reference.

FIELD

The present disclosure relates generally to the field of medical devices. In particular, the present disclosure relates to devices, systems, and methods to facilitate positioning an elongate member at a target site within a body lumen.

BACKGROUND

A variety of medical devices are positioned within a body lumen for diagnostic or therapeutic purposes. For example, an endoscopy is a procedure using an endoscope to look inside a body. Typically, an endoscopy procedure utilizes an elongate member (e.g., an endoscope) to access, examine, or interact with the interior of a hollow organ or cavity of a body for diagnostic or therapeutic purposes. The endoscope typically has direct visualization for viewing inside the body and/or may be equipped with ultrasound view capability. Such scopes have a profile diameter that allow the scope to be inserted into larger body lumens (e.g., GI tract or trachea) of a certain diameter. For example, one type of endoscope, a bronchoscope can be used for visualizing the inside of the airways, up to a certain generation of airway having a diameter that can accommodate the diameter of the bronchoscope, for diagnostic and therapeutic purposes. The bronchoscope is inserted into the airways, such as through a mouth, nose, or tracheostomy. This may allow the practitioner to examine the patient's airways for abnormalities such as foreign bodies, bleeding, tumors, or inflammation. Sometimes a biopsy may be taken from inside the lungs. At a certain higher generations of airways, the diameter of the airway becomes too narrow to accommodate conventional endoscopes, which presents the challenge for improved devices having means to accurately navigate, locate, and biopsy tissue within these smaller airways or within other lumens of minimal diameter.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one aspect, the present disclosure relates to an apparatus, comprising an elongate member, a lumen, and a first transducer. The elongate member may include an outer surface, a proximal end, a distal end, and at least one articulation joint disposed between the proximal end of the distal end. The lumen may have a first opening proximate the proximal end of the elongate member and a second opening proximate the distal end of the elongate member. The first transducer may include a phased array sensor disposed proximate the distal end of the elongate member.

In some embodiments, a field of view of the phased array sensor extends from the outer surface of the elongate member. In various embodiments, the second opening of the lumen is disposed in the outer surface of the elongate member. In various such embodiments, the lumen includes a ramp configured to direct an instrument into a field of view of the phased array sensor when the instrument extends through the lumen and out of the second opening of the lumen. In some such embodiments, the ramp includes a multiple-radius bend. Many embodiments include a second transducer including a position tracking sensor. In many such embodiments, the position tracking sensor comprises a magnetic tunnel junction. Some such embodiments include a third transducer including an optical imaging sensor. In various further such embodiments, at least one of the first, second, and third transducers is mounted on a flexible circuit board. Several embodiments include a second transducer including an optical imaging sensor. In several such embodiments, a field of view for the phased array sensor extends from the outer surface of the elongate member and a field of view for the optical imaging sensor extends from the distal end of the elongate member. In some such embodiments, the optical imaging sensor is mounted on the distal end of the elongate member. In various embodiments, the at least one articulation joint comprises a first articulation joint and a second articulation joint, wherein a direction of articulation of the first articulation joint is orthogonal to a direction of articulation of the second articulation joint. In many embodiments, the at least one articulation joint comprising a first articulation joint and a second articulation joint, wherein the second opening of the lumen is disposed between the first and second articulation joints. In some embodiments, a first portion of the phased array sensor is disposed proximal of the second opening of the lumen and a second portion of the phased array sensor is disposed distal of the second opening of the lumen.

In another aspect, the present disclosure relates to a system, comprising an elongate member, a lumen, a first transducer, and a controller. The elongate member may include an outer surface, a proximal end, and a distal end. The lumen may have a first opening proximate the proximal end of the elongate member and a second opening proximate the distal end of the elongate member. The first transducer may include a phased array sensor disposed proximate the distal end of the elongate member. The controller may be communicatively coupled to the first transducer and configured to generate an image based on signals received from the first transducer.

In some embodiments, a field of view of the phased array sensor extends from the outer surface of the elongate member. In various embodiments, the second opening of the lumen is disposed in the outer surface of the elongate member. In many embodiments, the at least one articulation joint comprises a first articulation joint and a second articulation joint, wherein a direction of articulation of the first articulation joint is orthogonal to a direction of articulation of the second articulation joint.

In yet another aspect, the present disclosure relates to a method. The method including inserting an elongate member into a body lumen, the elongate member comprising an outer surface, a proximal end, a distal end, at least one articulation joint disposed between the proximal end and the distal end, and a lumen having a first opening proximate the proximal end of the elongate member and a second opening proximate the distal end of the elongate member; generating a first image with a first transducer, the first transducer comprising a phased array sensor disposed proximate the distal end of the elongate member; and extending a tool out of the second opening of the lumen based on the image, wherein the second opening of the lumen is located in the outer surface of the elongate member.

In some embodiments, the method includes actuating an articulation joint of the at least one articulation joint to navigate to a target site. In various embodiments, the method includes generating a second image with the first transducer, wherein the second image is generated before the first image; and rotating the elongate member based on the second image to align the second opening of the lumen with a target site.

In yet another aspect, the present disclosure relates to a method. The method including mounting first and second transducers to a flexible circuit board; and positioning the first transducer relative to the second transducer with a low-pressure epoxy potting process that produces a transducer subassembly comprising the first transducer, the second transducer, and at least a portion of the flexible circuit board.

In some embodiments, the method includes forming a lens attachment feature on the transducer subassembly in the low-pressure epoxy potting process. In some such embodiments, the method includes forming a transducer lens in a molding process; and attaching the transducer lens to the transducer subassembly.

BRIEF DESCRIPTION OF THE SEVERAL VIEWS OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. In will be appreciated that various figures included in this disclosure may omit some components, illustrate portions of some components, and/or present some components as transparent to facilitate illustration and description of components that may otherwise appear hidden. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
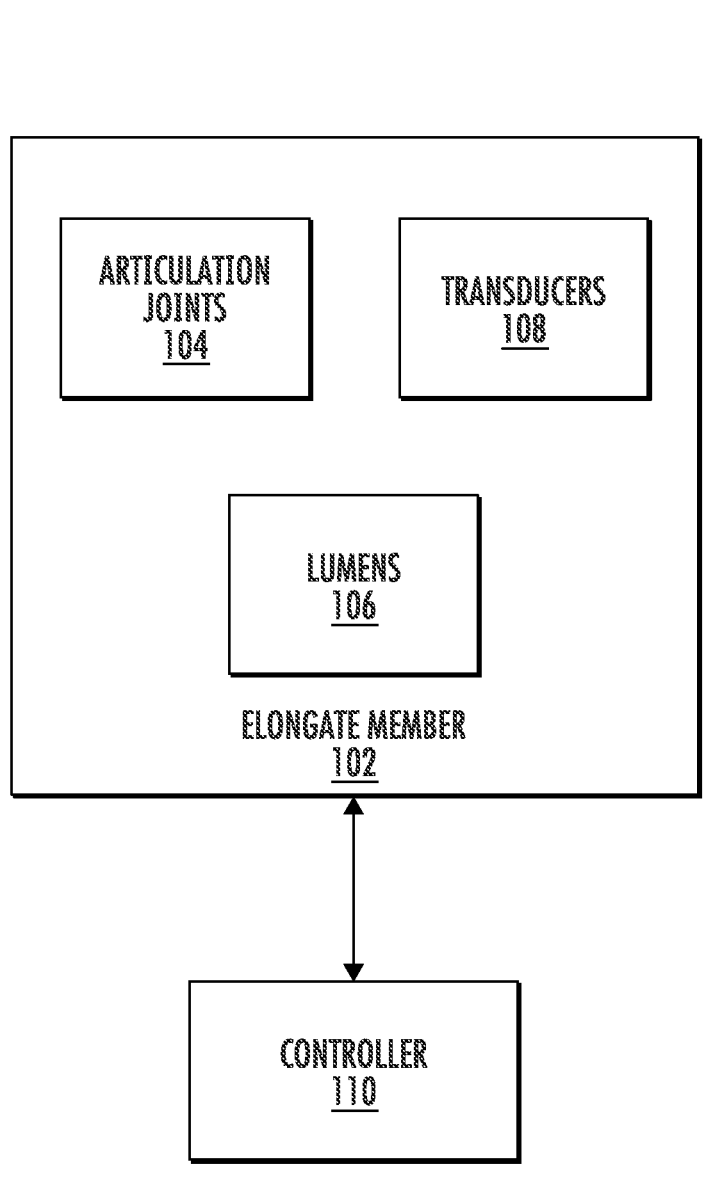
FIG. 1 illustrates an exemplary medical device according to one or more embodiments disclosed hereby.

The present disclosure relates generally to medical devices for positioning elongate members at a target site within a body lumen, such as for acquiring a biopsy from a peripheral airway. In various embodiments, the elongate member may include one or more articulation joints for maneuvering, one or more transducers for localizing, and one or more lumens for delivering instruments to the target site. Some embodiments are particularly directed to a medical device that guides an operator to a target site, confirms the location of the target site, and enables a biopsy to be taken from and/or a therapy to be delivered to the target site. For example, a position tracking sensor (e.g., an inductive or tunnel-magnetoresistance (TMR) sensor) may be utilized to guide the medical device to the target site, a phased array sensor (e.g., a phased array of ultrasound imaging elements) may be utilized to confirming proper positioning at the target site, a biopsy needle inserted through a lumen may be utilized to acquire a sample from the target site. In some such examples, the medical device may also include an optical imaging sensor to assist in guiding the medical devices to the target site and/or confirming proper positioning at the target site. Additionally, one or more of these features may be combined into an elongate member with small enough dimensions to access narrow peripheral body lumens. In some embodiments, the medical device enables a therapeutic probe (e.g., an ablation probe) to be delivered and positioned at or within a target site, such as a lesion. In some such embodiments, the therapeutic probe may be inserted through the lumen to deliver a therapy to the target site after a biopsy needle has be inserted through the lumen to acquire a sample for confirmation. These and other embodiments are described and claimed.

Many challenges face medical devices for positioning elongate members at target sites within a body lumen, such as external dimensions that limit access to narrow body lumens. For example, endobronchial ultrasound (EBUS) scopes are too large (e.g., OD over 4 mm) to reach into peripheral portions of body lumens (e.g., peripheral airways), where suspected cancerous nodules are commonly located. Electromagnetic (EM) bronchoscopy may be used to locate targets sites (e.g., suspected cancerous nodules in the periphery of the airway). However, errors, such as those introduced through a combination of metallic distortion and pre-operative computerized tomography (CT) scans to intra-operative patient position divergence, can prevent confirmation of proper positioning at a target site. Accordingly, operators typically rely on other technologies, such as reusable, single element (rotational) ultrasound probes, used in conjunction with EM bronchoscopy to confirm proper positioning at a target site. However, these probes are non-steerable and fill an entire lumen (e.g., working channel), necessitating removal of the probe before an instrument (e.g., a biopsy needle) can be inserted into the lumen. Further, device exchanges can contribute to tip movement and removal of the ultrasound probe prevents confirming the location of the elongate member once the instrument has been inserted, leading to a number of challenges, such as lower diagnostic yield for biopsies or inaccurate positioning of a probe during therapy. Inaccurate positioning of a probe (e.g., ablation probe) during therapy can result in the operator not achieving expected therapeutic results, such as a target margin. Such limitations can drastically reduce the usability and applicability medical devices for positioning elongate member at target sites, contributing to inefficient devices with limited capabilities. It is with these considerations in mind that a variety of advantageous medical outcomes may be realized by the devices, systems, and methods of the present disclosure.

The following detailed description should be read with reference to the drawings, which depict illustrative embodiments. The present disclosure is not limited to the particular embodiments described, as such embodiments may vary. The terminology used herein is for the purpose of describing particular embodiments only and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure may be described with specific reference to medical devices and systems and procedures for treating the gastrointestinal system, it should be appreciated that such medical devices and methods may be used to treat tissues of the abdominal cavity, digestive system, urinary tract, reproductive tract, respiratory system, cardiovascular system, circulatory system, and the like. The structures and configurations, and methods of deploying, in order to stabilize, maintain, and/or otherwise facilitate fluid flow paths may find utility beyond treatments discussed herein.

As used herein, "proximal end" refers to the end of a device that lies closest to the user (medical professional or clinician or technician or operator or physician, etc., such terms being used interchangeably herein without intent to limit, and including automated controller systems or otherwise) along the device when introducing the device into a patient, and "distal end" refers to the end of a device or object that lies furthest from the user along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified. The recitation of numerical ranges or values by endpoints includes all numbers within that range, including the endpoints (e.g. 1 to 5 includes 1, 1.5, 2, 2.75, 3, 3.80, 4, and 5), and fractions thereof.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Although endoscopes and endoscopic systems are referenced herein, reference to endoscopes, endoscopic systems, or endoscopy should not be construed as limiting the possible applications of the disclosed aspects. For example, the disclosed aspects may be used in conjunction with duodenoscopes, bronchoscopes, ureteroscopes, colonoscopes, catheters, diagnostic or therapeutic tools or devices, or other types of medical devices or systems.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIG. 1 illustrates a medical device 100 according to one or more embodiments disclosed hereby. Medical device 100 may include an elongate member 102 and a controller 110. The elongate member 102 may include one or more articulation joints 104, one or more lumens 106, and one or more transducers 108. As will be described in more detail below, the medical device 100 may provide functionality that enables guidance to a target site, confirmation of location at the target site, and enables an instrument to be delivered to the target site. In some embodiments, FIG. 1 may include one or more components that are the same or similar to one or more other components of the present disclosure. Further, one or more components of FIG. 1, or aspects thereof, may be incorporated into other embodiments of the present disclosure, or excluded from the described embodiments, without departing from the scope of this disclosure. For example, embodiments of medical device 100 may exclude controller 110 without departing from the scope of this disclosure. Still further, one or more components of other embodiments of the present disclosure, or aspects thereof, may be incorporated into one or more components of FIG. 1, without departing from the scope of this disclosure. Embodiments are not limited in this context.

In various embodiments, medical device 100 may enable reliable and accurate access to peripheral portions of a body lumen, such as a peripheral airway. In many embodiments, the access to peripheral portions of a body lumen may be utilized to acquire a biopsy of target tissue (e.g., a suspected cancerous nodule) or deliver a treatment or therapy to target tissue. Accordingly, the elongate member 102 may have an outer profile small enough to fit into peripheral portions of a body lumen while still providing one or more of real-time localization of the elongate member 102, real-time imaging within the peripheral portions of the body lumen, steerability of the elongate member 102, and delivery of an instrument to a target site without interfering with the real-time localization or the real-time imaging.

In some embodiments, the outside diameter of the elongate member 102 may not exceed 5 mm. In other embodiments, the outside diameter (OD) of the elongate member 102 may not exceed 4.2 mm. In some embodiments, the elongate member 102 may include a taper near the distal end to facilitate navigation and/or entry into small diameter body lumens, such as peripheral airways. One or more devices or embodiments herein may be sized and/or configured to be utilized for diagnostic or therapeutic purposes, such as in one or more of pulmonary, cardiac, endoscopic, and urologic applications. In various embodiments, the outer profile of the elongate member may be isodiametric with atraumatic (e.g., radiused) edges. Embodiments of medical device 100 may be utilized in a variety of applications, such as peripheral lung navigation, peripheral lung biopsy, peripheral lung ultrasound reconstruction, and peripheral lung treatment.

In several embodiments, transducers 108 may generally refer to a device that converts energy from one form into another. In many embodiments, each of the transducers may operate to convert one or more electrical signal to one or more physical quantities (e.g., energy, force, torque, light, motion, position, etcetera) and/or convert one or more physical quantities to one or more electrical signals. For example, a transducer may include one or more of an imaging sensor, a phased array sensor, a position sensor, a light emitting diode, a pressure sensor, an actuator, an inductive sensor, a TMR sensor, a fiber-optic sensor, an electromagnetic position sensor, or the like.

Figure 2A:
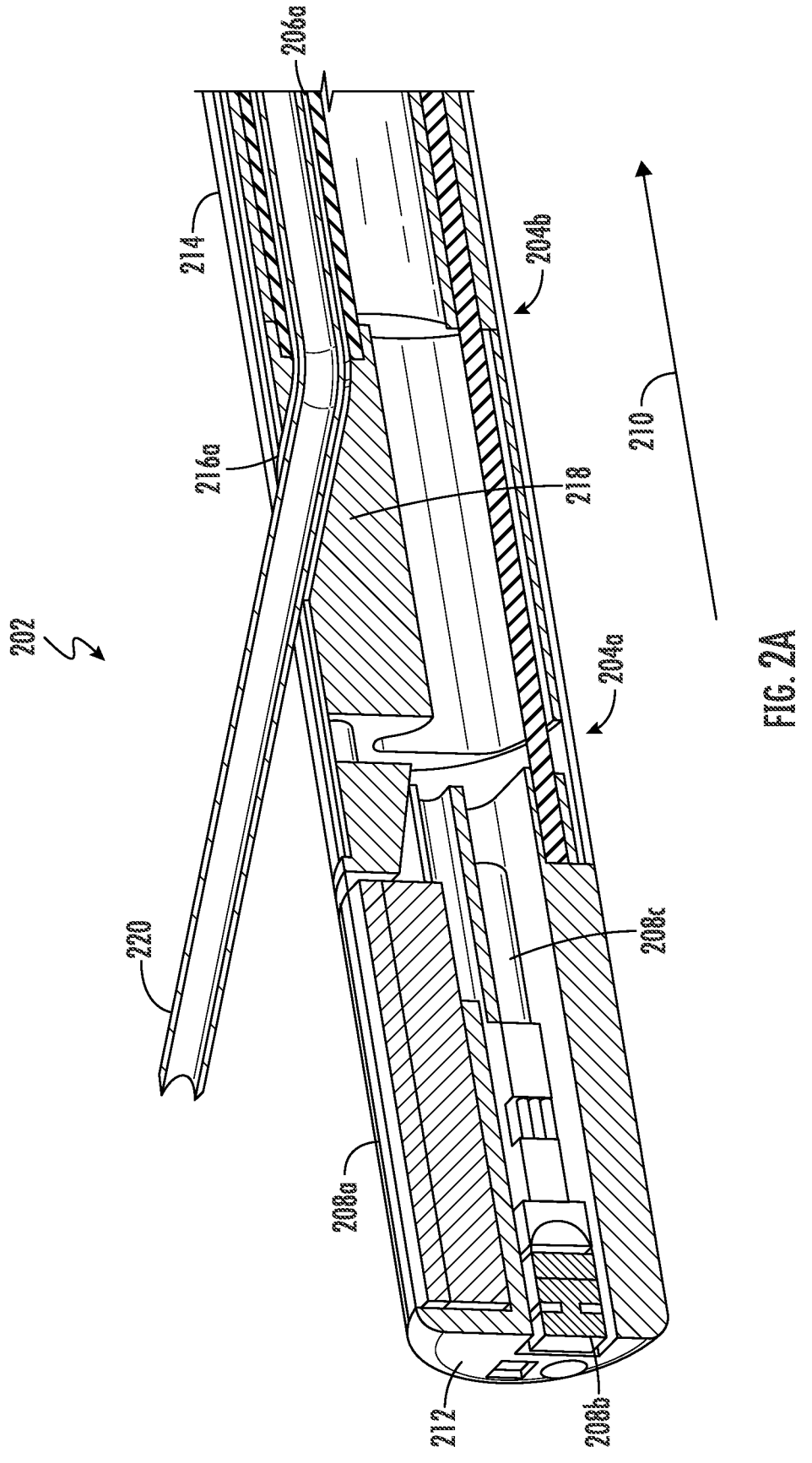
FIGS. 2A-2C illustrate various aspects of an exemplary elongate member according to one or more embodiments disclosed hereby.
Figure 2B:
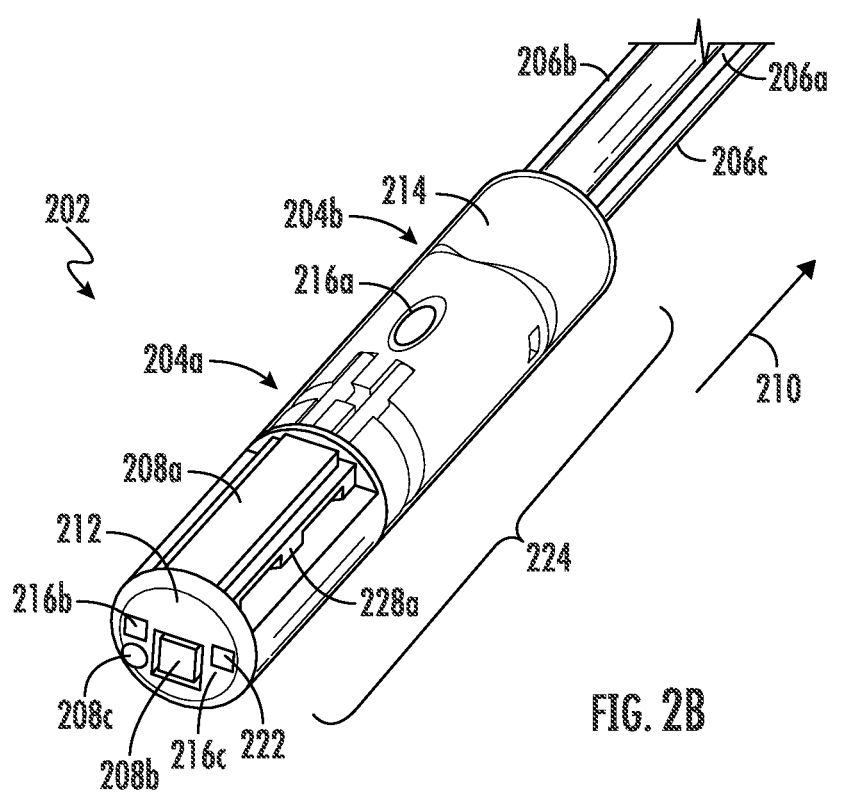
Figure 2C:
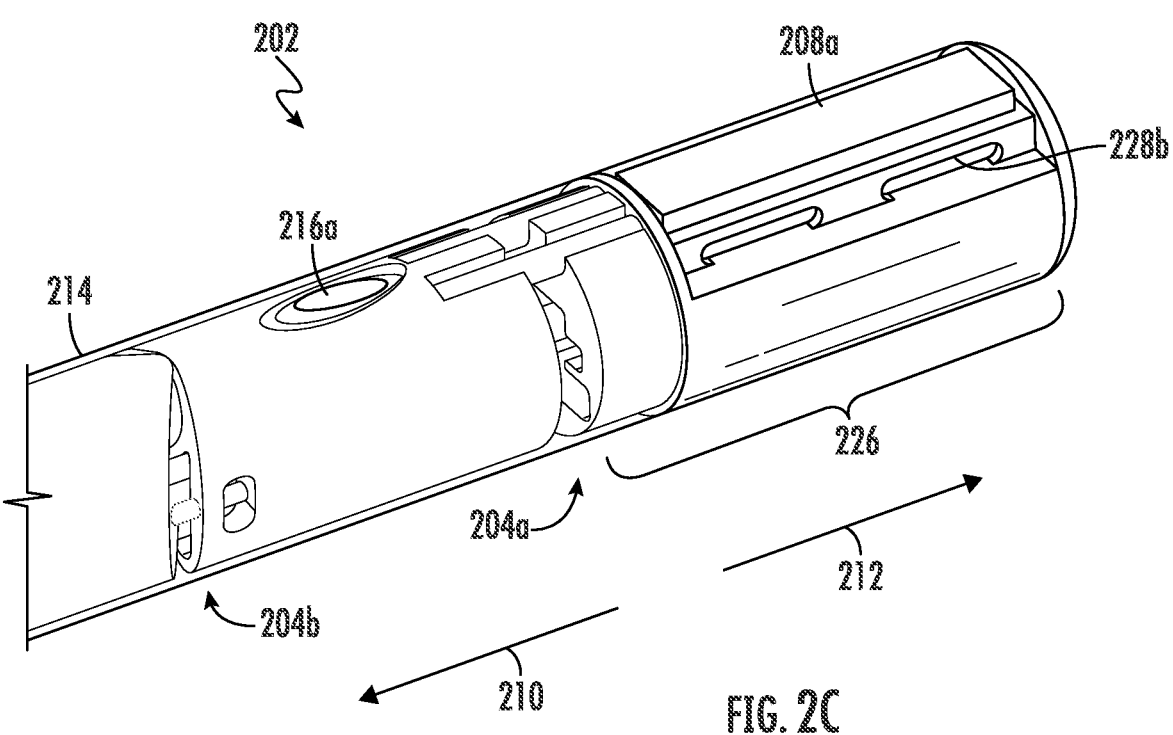

FIGS. 2A-2C illustrate various aspects of an elongate member 202 according to one or more embodiments disclosed hereby. More specifically, FIG. 2A includes a cross-sectional view of a distal portion of elongate member 202 in conjunction with instrument 220; FIG. 2B includes a perspective view of a distal portion of elongate member 202 including machined component 224; and FIG. 2C includes another perspective view of a distal portion of elongate member 202 including transducer subassembly 226. The elongate member 202 has a proximal end 210, a distal end 212, an outer surface 214, and includes articulation joints 204a, 204b, lumens 206a, 206b, 206c, transducers 208a, 208b, 208c, opening 216a, opening 216b, ramp 218, light 222, and lens attachment features 228a, 228b. In some embodiments, FIGS. 2A, 2B, and/or 2C may include one or more components that are the same or similar to one or more other components of the present disclosure. For example, elongate member 202 may be the same or similar to elongate member 102. Further, one or more components of FIGS. 2A, 2B, and/or 2C, or aspects thereof, may be incorporated into other embodiments of the present disclosure, or excluded from the described embodiments, without departing from the scope of this disclosure. For example, embodiments of elongate member 202 may exclude transducer 208b without departing from the scope of this disclosure. Still further, one or more components of other embodiments of the present disclosure, or aspects thereof, may be incorporated into one or more components of FIGS. 2A, 2B, and/or 2C, without departing from the scope of this disclosure. Embodiments are not limited in this context.

Referring to FIG. 2A, the distal end 212 of elongate member 202 may include transducer 208a for side, or radial, imaging, transducer 208b for forward imaging, and transducer 208c for electromagnetic position sensing. In some embodiments, a plurality of electromagnetic position sensors may be disposed along the length of the elongate member 202. For example, position sensing transducers may be in a plurality of sections of the elongate member 202 separated by articulations articulation joints 204a, 204b to facilitate determining (e.g., by controller 110) the movement or position of the sections with respect to each other. In some embodiments, fiber-optic shape sensing may be utilized. For example, one or more optical fibers may extend along one or more portions of the length of the elongate member 202. In such example, the effects on light (e.g., reflection, refraction, absorption, polarity, etcetera) passing through the one or more optical fibers can be used to determine the shape of the elongate member. In some embodiments, fiber-optic shape sensing may be used to continuously determine the shape along the entire length of the elongate member 202.

Opening 216a may be disposed in the outer surface 214 of elongate member 202 and lumen 206a may terminate at opening 216a. In various embodiments, lumen 206a may comprise a working channel. In the illustrated embodiments, instrument 220 is inserted through the lumen 206a and extends out of opening 216a. In various embodiments, the lumen 206a may be sized to receive an instrument with an outside diameter of at least 1.067 mm (e.g., a 19-gauge needle). Ramp 218 may be configured to direct instrument 220 into a field of view of the transducer 208a when the instrument 220 extended through the lumen 206a and out of opening 216a.

In various embodiments, the angle of the ramp 218 may be between 0 and 90 degrees with respect to the longitudinal axis of the elongate member 202. In many embodiments, higher angles may improve nodule targeting (e.g., an eccentric lesion), but make actuation more difficult. For example, the higher the angle of the ramp 218, the larger the longitudinal force required to extend the instrument 220 up the ramp 218 and out of opening 216a. Further, higher angles may require the needle to extend further out and away from elongate member 202 to enter the field of view of the transducer 208a, limiting applicability to body lumens with larger diameters. Conversely, lower angles may require the elongate member 202 to be located closer to a target nodule, making it difficult to acquire biopsy samples from an eccentric nodule and/or further below the surface of the target nodule. Accordingly, the ramp angle may be selected based on a particular application. In one or more embodiments, the ramp angle may be greater than or equal to 3 degrees and less than or equal to 20 degrees. For instance, the angle of ramp 218 may be 15 degrees. In another instance, the angle of ramp 218 may be 10 degrees.

Referring to FIG. 2B, openings 216b, 216c may be disposed in the distal end 212 of elongate member 202. Further, lumen 206b may terminate at opening 216b and lumen 206c may terminate at opening 216c. In some embodiments, lumens 206a, 206b may provide suction and/or fluid channels to the distal end 212 of elongate member 202. In the illustrated embodiment, opening 216b comprises a suction port (e.g., for clearing mucus from the face of transducer 208b) and light 222 is disposed in opening 216c with wires for light 222 extending through lumen 206c. It will be appreciated that light 222 may plug opening 216c or be integrally formed into the elongate member 202 (e.g., as part of an epoxy potting process). In some embodiments, lumen 206c may comprise encapsulated wires for light 222.

In various embodiments, another light may be disposed in opening 216b instead of using opening 216b as a suction port. The light 222 may include a light emitting diode that emits light at a frequency the transducer 208b is able to detect. For example, transducer 208b may comprise an optical imaging sensor and light 222 may emit visible light.

Portions of elongate member 202 are removed or transparent in FIG. 2B to better illustrate lumens 206a, 206b, 206c and machined component 224. In some embodiments, a flexible and/or elastic member extends from the proximal end of machined component 224 to the proximal end 210 of elongate member 202. In some such embodiments, the flexible and/or elastic member may include the illustrated portions of lumens 206a, 206b, 206c. In several embodiments, the machined component 224 may form the portions of lumens 206a, 206b, 206c extending from the proximal end of machined component 224 to openings 216a, 216b, 216c. The machined component 224 may provide a single bend radius for passing tools (e.g., instrument 220) out of opening 216a in outer surface 214 at a predetermined angle and/or controlled distance from the face of the transducer 208a. In various embodiments, transducer 208a may include a phased array that emits and detects ultrasonic pulses.

In several embodiments, the transducer subassembly 226 may comprise the portion of elongate member 202 that is distal to articulation joint 204. In various embodiments, the transducer subassembly 226 may include one or more lens attachment features. The lens attachment features may provide an anchor for attaching a lens (e.g., for a phased array sensor). In the illustrated embodiment, lens attachment features 228a, 228b are disposed on either side of transducer 208a. Lens attachment features 228a, 228b may include a rail with one or more openings for receiving a corresponding portion of a lens or lens bracket. The lens may be constructed from an imaging compatible material, such as silicone for ultrasound imaging.

Referring to FIG. 2C, the opening 216a and transducer 208a may be maneuvered via articulation joints 204a, 204b. In various embodiments, the opening 216a may be disposed between articulation joints 204a, 204b and transducer 208a may be disposed between articulation joint 204a and distal end 212. The portion of elongate member 202 distal of articulation joint 204a may be referred to as the transducer subassembly 226. As will be discussed in more detail below, such as with respect to FIGS. 3A and 3B, articulation joints 204a, 204b may provide elongate member 202 with dual mode steerability that allows the transducer subassembly 226 to be moved independently of opening 216a. In many embodiments, a handle may be attached to the proximal end 210 of elongate member 202. As will be discussed in more detail below, such as with respect to FIGS. 5A-5C, in many such embodiments, the handle may enable an operator to actuate articulation joints 204a, 204b.

Figure 3A:
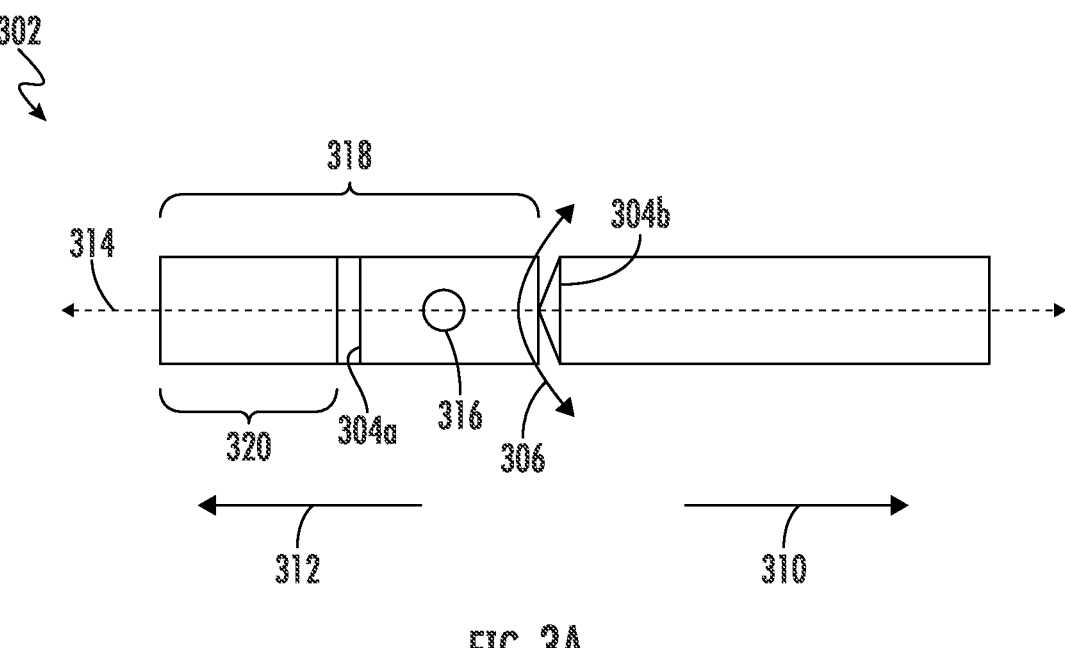
FIGS. 3A and 3B illustrate various aspects of exemplary articulation joints according to one or more embodiments disclosed hereby.
Figure 3B:
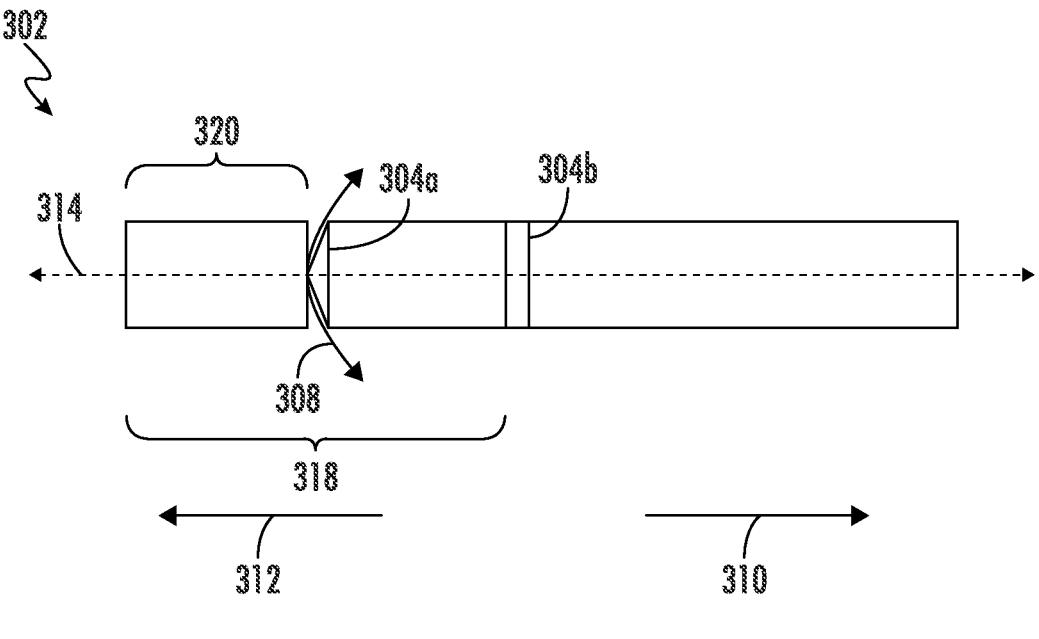

FIGS. 3A and 3B illustrate various aspects of articulation joints 304a, 304b in elongate member 302 according to one or more embodiments disclosed hereby. More specifically, FIG. 3A includes a top view of a distal portion of elongate member 302 with opening 316 and FIG. 3B includes a side view of the distal portion of elongate member 302. Elongate member 302 extends along a longitudinal axis 314 and includes a proximal end 310, a distal end 312, distal steering assembly 318 with transducer subassembly 320, and articulation joints 304a, 304b. Articulation joints 304a, 304b may be disposed between proximal end 310 and distal end 312 and opening 316 may be disposed between articulation joints 304a, 304b. Articulation joint 304a includes direction of articulation 306 and articulation joint 304b includes direction of articulation 308. In various embodiments, direction of articulation 306 may be orthogonal to direction of articulation 308. The articulation joints 304a, 304b may be configured to enable movement of transducer subassembly 320 independent of the distal steering assembly 318. In some embodiments, FIGS. 3A and/or 3B may include one or more components that are the same or similar to one or more other components of the present disclosure. For example, articulation joint 304a may be the same or similar to articulation joint 204a and articulation joint 304b may be the same or similar to articulation joint 204b. Further, one or more components of FIGS. 3A and/or 3B, or aspects thereof, may be incorporated into other embodiments of the present disclosure, or excluded from the described embodiments, without departing from the scope of this disclosure. Still further, one or more components of other embodiments of the present disclosure, or aspects thereof, may be incorporated into one or more components of FIGS. 3A and/or 3B, without departing from the scope of this disclosure. For example, transducers 208a, 208b may be incorporated into elongate member 302 without departing from the scope of this disclosure. Embodiments are not limited in this context.

In various embodiments, articulation joints 304a, 304b may enable dual mode steerability. Dual mode steerability may allow for bi-directional steering of the distal steering assembly 318 plus separate steerability of the transducer subassembly 320 independent of the portion of elongate member 302 including opening 316 between articulation joints 304a, 304b. The additional point of deflection of transducer subassembly 320 can enable the elongate member 302 to navigate around tighter bend radii and offsets additional length of transducer subassembly 320 due to size constraints of one or more of the transducers in the transducer subassembly 320 (e.g., due to the length of a phased array sensor with 48 ultrasound elements). In various embodiments, the additional point of deflection may enable one or more transducers in transducer subassembly 320 to contact, or be embedded in, the wall of a body lumen. As previously mentioned, in the illustrated embodiment, the transducer subassembly 320 may deflect in a direction that is orthogonal (e.g., offset 90 degrees) from steering of the entire distal steering assembly 318. However, in other embodiments, the transducer subassembly 320 may deflect in the same direction as the steering of the entire distal steering assembly 318.

In some embodiments, articulation joint 304a and/or articulation joint 304b may only bend past the longitudinal axis 314 in a first direction. For example, articulation joint 304a may bend past longitudinal axis 314 in a direction (e.g., towards the top of the page in FIG. 3B) without bending past longitudinal axis 314 in an opposite direction (e.g., towards the bottom of the page in FIG. 3B). As will be described in more detail below, such as with respect to FIG. 5C, elongate members may include one or more hard stops to limit the movement of articulation joints to a predetermined range. In some embodiments, limiting the movement of articulation joints to a predetermined range may ensure components are not prevented from functioning properly and/or an instrument can still be inserted through a lumen of the elongate member without damaging itself or the instrument.

Figure 4:
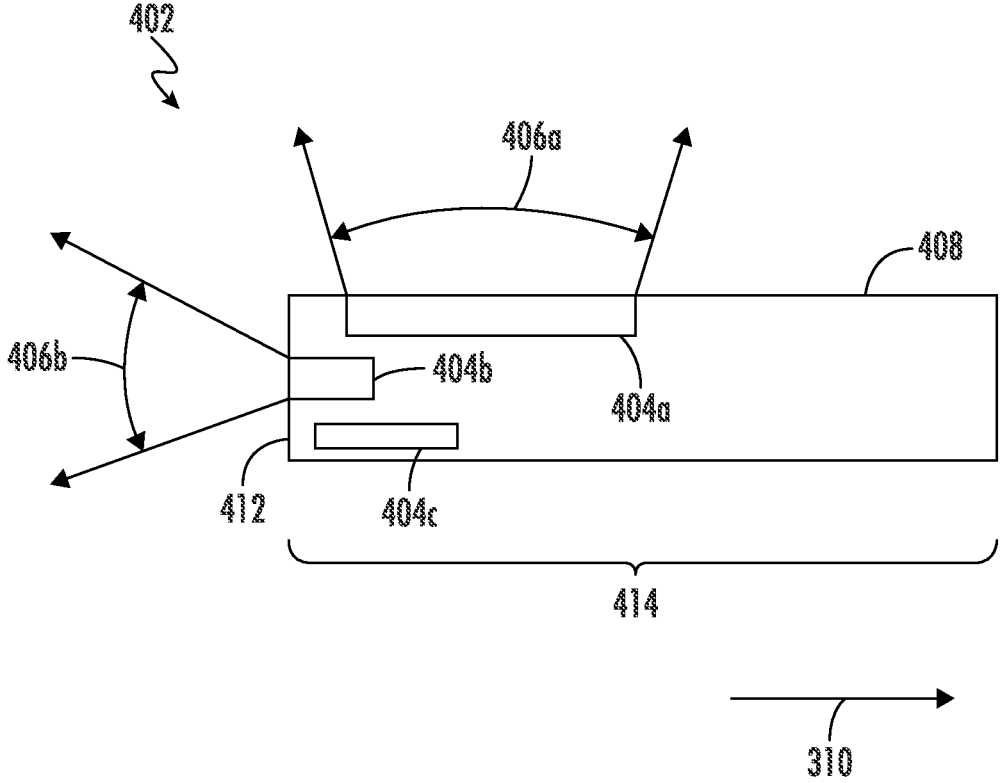
FIG. 4 illustrates various aspects of exemplary transducers according to one or more embodiments disclosed hereby.

FIG. 4 illustrates various aspects of exemplary transducers 404a, 404b according to one or more embodiments disclosed hereby. The illustrated embodiment includes a side view of a transducer subassembly 414 of an elongate member 402 having an outer surface 408, a proximal end 410, a distal end 412, transducer 404a with field of view 406a, transducer 404b with field of view 406b, and transducer. Accordingly, transducers 404a, 404b may be imaging sensors. For example, transducer 404a may be a phased array sensor of at least two elements and transducer 404b may be an optical imaging sensor. In various embodiments, the transducer 404a may enable side, or radial, imaging and the transducer 404b may enable forward imaging. In several embodiments, the field of view 406a of transducer 404b may extend from the outer surfaces 408 of elongate member 402 and the field of view 406b of transducer 404b may extend from the distal end 412 of elongate member 402. In some embodiments, the field of view 406a may be orthogonal to the field of view 406b. In various embodiments, transducer 404c may comprise a position tracking sensor, such as an electromagnetic position sensor (e.g., an inductive or TMR sensor). In some embodiments, FIG. 4 may include one or more components that are the same or similar to one or more other components of the present disclosure. For example, transducer 404a may be the same or similar to transducer 208a and transducer 404b may be the same or similar to transducer 208b. Further, one or more components of FIG. 4, or aspects thereof, may be incorporated into other embodiments of the present disclosure, or excluded from the described embodiments, without departing from the scope of this disclosure. For example, field of view 406a may be incorporated into transducer 208a and field of view 406b may be incorporated into transducer 208b. Still further, one or more components of other embodiments of the present disclosure, or aspects thereof, may be incorporated into one or more components of FIG. 4, without departing from the scope of this disclosure. For example, lumen 206a with opening 216a may be incorporated into elongate member 402. Embodiments are not limited in this context.

In various embodiments, one or more of the transducers 404a, 404b, 404c, may be mounted to a flexible circuit board. In various such embodiments, two or more of the transducers 404a, 404b, 404c may be mounted to a common flexible circuit board. For example, transducer 404b and transducer 404c may be mounted to a common flexible circuit board. In some such examples, transducer 404b may include a front facing optical imaging sensor (e.g., camera) and transducer 404c may include a TMR based position sensor. In some embodiments, one or more of the transducers 404a, 404b, 404c may be mounted to a flexible circuit board that at least partially wraps around the transducer subassembly 414, such as proximate the outer diameter of the transducer subassembly. In various embodiments, the flexible circuit board is at least partially encapsulated, such as in a potting material. In some embodiments, a low-pressure epoxy potting method may be utilized.

In many embodiments, transducer 404c may comprise a 6 degrees of freedom (DOF) sensor. In various embodiments, transducer 404c may be cylindrical with a length less than 9 mm and a diameter less than 1.5 mm. In one embodiment, transducer 404c may include a cylindrical TMR sensor with an 8 mm length and a 0.65 mm diameter. In some embodiments, transducer 404c may include, or be mounted to, a semi-circular, or 'C' shaped flexible circuit board. In various embodiments, the transducer 404c may be mounted to either the inside or the outside of the transducer subassembly 414. In many embodiments, the configuration and dimensions of the components of elongate member 402 may enable the elongate member 402 to access peripheral body lumens, such as peripheral airways. For example, an outer diameter of less than 2 mm, such as 1.5 mm, may be suitable for peripheral airways. However, different suitable dimensional ranges and limits may be applicable based on a desired application.

In many embodiments, the flexible circuit board of transducer 404c may, at least partially, wrap around the transducer subassembly 414, such by being embedded in the transducer subassembly proximate the outer diameter. In several embodiments, the flexible circuit the transducer 404c includes, or is mounted to, may be the same or different than a flexible circuit one or more other transducers are mounted to. In one embodiment, the flexible circuit may include connection pads that allow signals from other transducers to traverse the flexible circuit board.

In several embodiments, the flexible circuit may be shaped according to available space and size constraints. In various embodiments, the flexible circuit may be manufactured in a flat configuration and formed into the desired shape using a secondary potting application. In other embodiments, the flexible circuit may be manufactured in the targeted end shape. In some embodiments, the transducer 404c may be reflowed into the elongate member 402. For example, the ability to shape transducer 404c comprising a 6-DOF sensor and wrap the transducer 404c around an outer profile of the transducer subassembly 414 can enable the transducer 404c to be reflowed into the elongate member 402 and avoid taking up excessive space in the tip and/or cross-sectional area of the device.

In several embodiments, the elongate member 402 may be manufactured as a single use device (SUD). Accordingly, a variety of epoxies, polymers, and/or composites may be utilized, such as in place of metal for some components. In many embodiments, the transducer subassembly 414 may be manufactured using of a low-pressure epoxy potting process to position transducer 404b (e.g., front facing camera) and transducer 404c (e.g., TMR based position sensor). In many such embodiments, features to securely attach a transducer lens (e.g., lens attachment features 228a, 228b) may also be included in the design of the low-pressure epoxy component. In various embodiments, the transducer lens (e.g., for lens attachment features 228a, 228b) may be formed in a molding process, such as a silicone, or other ultrasound imaging compatible material, molding process. In several embodiments, the low-pressure epoxy potting process may be the first step in a two-part manufacturing process while formation of the lens may be the second step in the two-part manufacturing process.

Figure 5A:
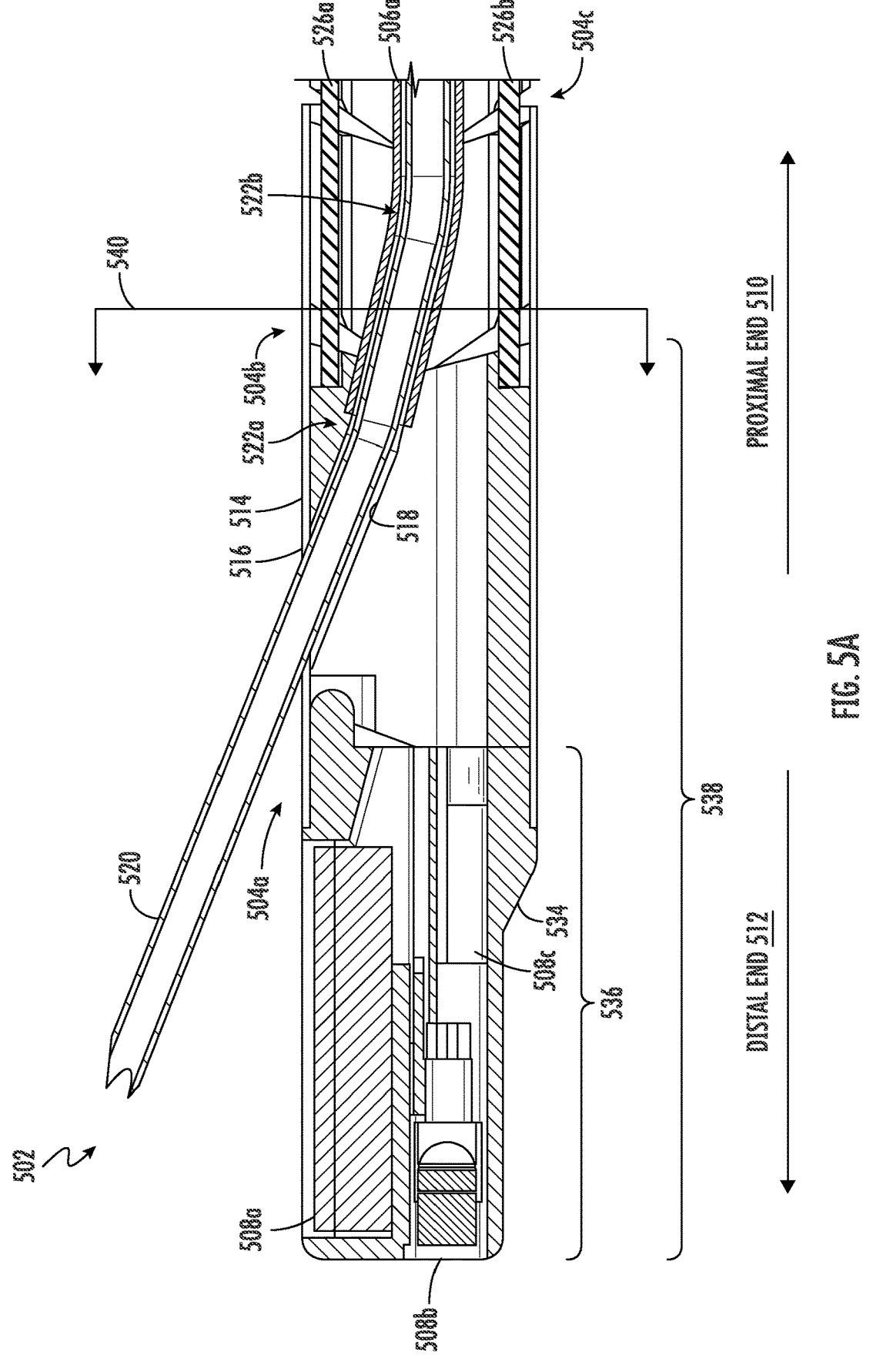
FIGS. 5A-5C illustrate various aspects of an exemplary elongate member according to one or more embodiments disclosed hereby.
Figure 5B:
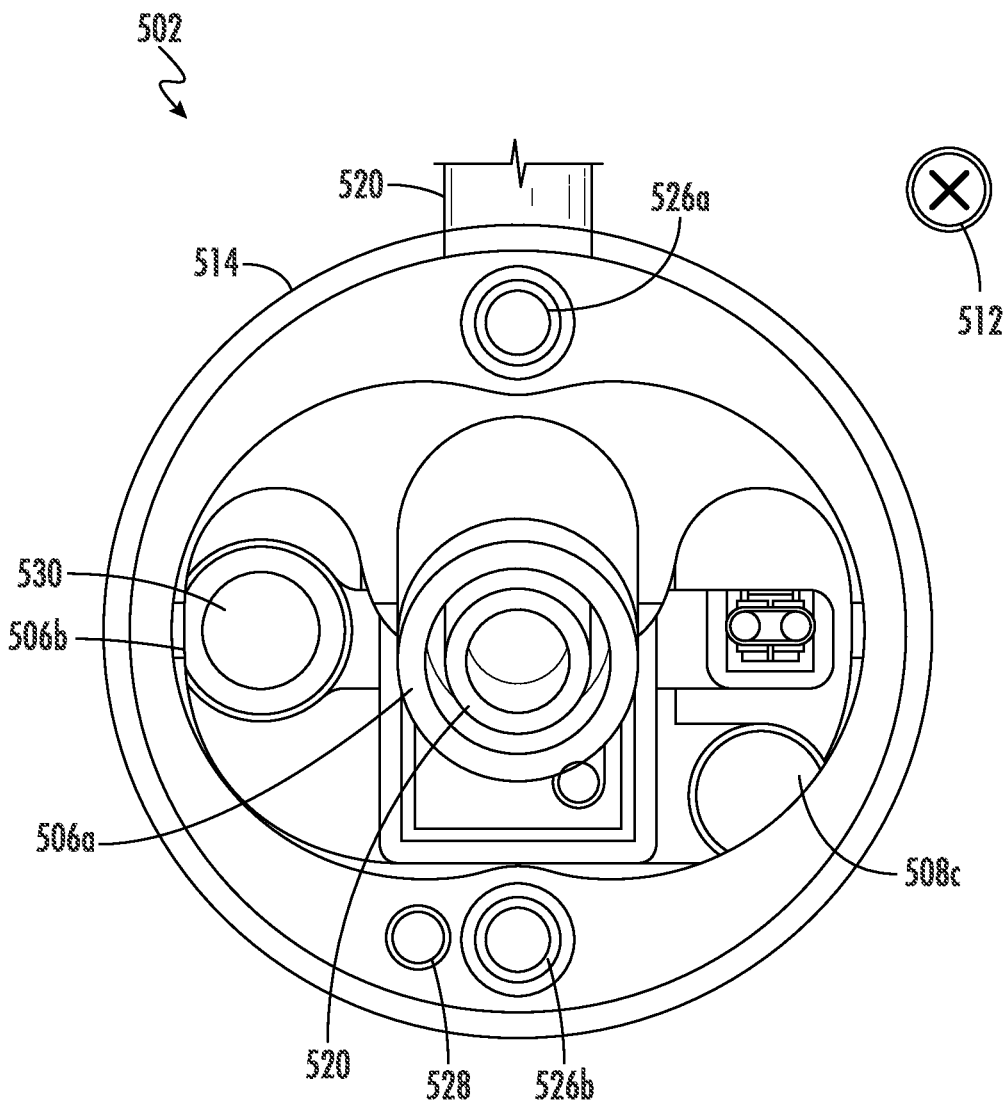
Figure 5C:
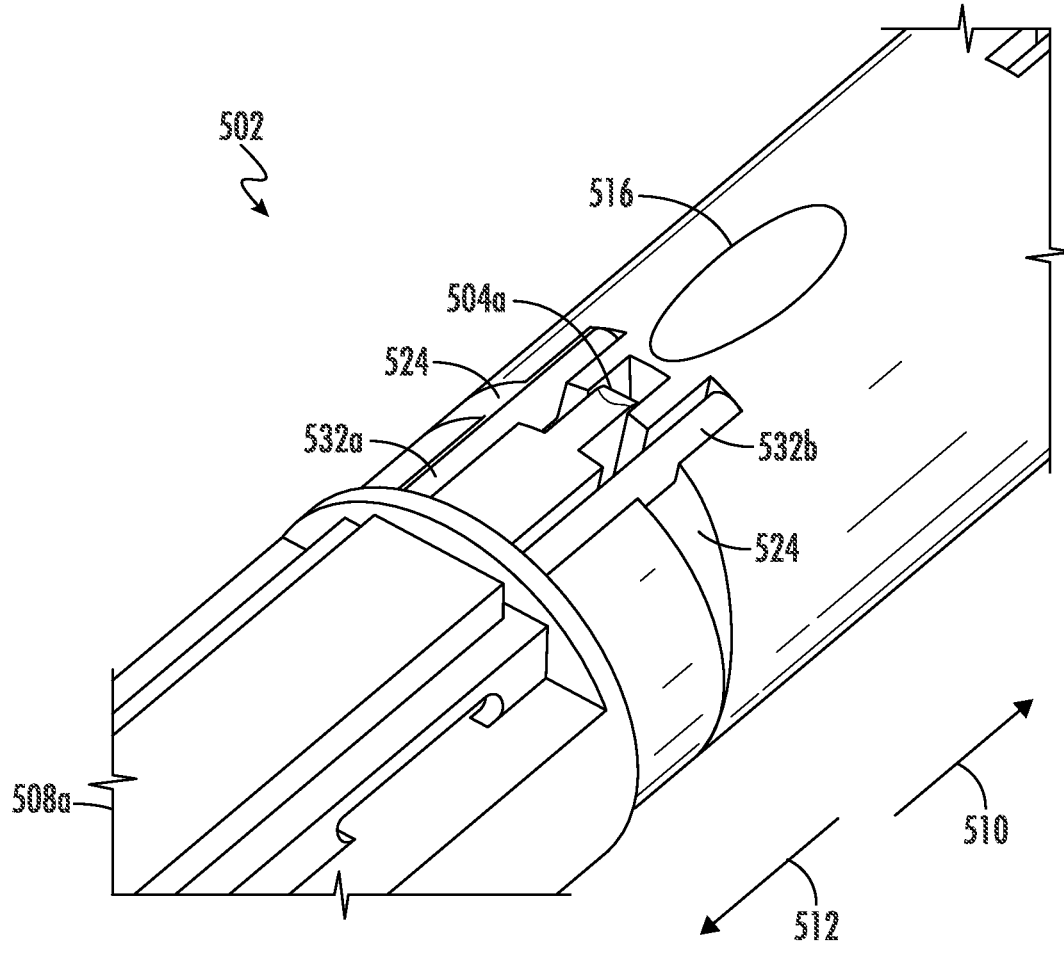

FIGS. 5A-5C illustrate various aspects of an elongate member 502 according to one or more embodiments disclosed hereby. More specifically, FIG. 5A includes a cross-sectional view of a distal portion of elongate member 502, including distal steering assembly 538 with transducer subassembly 536, in conjunction with biopsy needle 520; FIG. 5B includes a transverse cross-sectional view of a distal portion of elongate member 502 at cutting plane 540; and FIG. 5C includes a perspective view of a distal portion of elongate member 502. The elongate member 502 has a proximal end 510, a distal end 512, an outer surface 514, and includes articulation joints 504a, 504b, 504c, lumens 506a, 506b, phased array sensor 508a, optical imaging sensor 508b, position tracking sensor 508c, opening 516, ramp 518 with bend radii 522a, 522b, hard stops 524, steering wire 526a, steering wire 526b, pull wire 528, suction channel 530, actuation members 532a, 532b, and taper 534. In some embodiments, FIGS. 5A, 5B, and/or 5C may include one or more components that are the same or similar to one or more other components of the present disclosure. For example, transducer subassembly 536 may be similar to transducer subassembly 320. Further, one or more components of FIGS. 5A, 5B, and/or 5C, or aspects thereof, may be incorporated into other embodiments of the present disclosure, or excluded from the described embodiments, without departing from the scope of this disclosure. For example, embodiments of elongate member 502 may exclude optical imaging sensor 508*b* without departing from the scope of this disclosure. Still further, one or more components of other embodiments of the present disclosure, or aspects thereof, may be incorporated into one or more components of FIGS. 5A, 5B, and/or 5C, without departing from the scope of this disclosure. For example, light 222 may be incorporated into elongate member 502 without departing from the scope of this disclosure. Embodiments are not limited in this context.

Generally, the arrangement of components in elongate member 502 may be similar to the arrangement of components in elongate member 202. Additionally, or alternatively, elongate member 502 includes, or illustrates, a taper 534 in the outer surfaces 514, a third articulation joint 504*c*, a ramp 518 with dual bend radii 522*a*, 522*b*, hard stops 524, steering wires 526*a*, 526*b*, pull wire 528, suction channel 530, and actuation members 532*a*, 532*b*. Some embodiments may include phased array sensor 508*a* without including optical imaging sensor 508*b* and/or position tracking sensor 508*c*. Various embodiments may include an opening for biopsy needle 520 in the distal end 512 of elongate member 502 instead of opening 516.

As discussed above, the ramp angle may be greater than or equal to 3 degrees and less than or equal to 20 degrees. For instance, the angle of ramp 518 may be 15 degrees. In another instance, the angle of ramp 518 may be 10 degrees. However, in ramp 518, the total angle of the ramp may be divided between bend radii 522*a*, 522*b*. For example, bend radius 522*b* may deflect from a longitudinal axis of elongate member 502 by an angle of 7.5 degrees and bend radius 522*a* may deflect another 7.5 degrees for a total angle of 15 degrees. In another example, bend radius 522*b* may deflect from a longitudinal axis of elongate member 502 by an angle of 4 degrees and bend radius 522*a* may deflect another 6 degrees for a total angle of 10 degrees.

In various embodiments, the ramp 518 may include at least two different bend radii to enable larger diameter tools (e.g., 19G biopsy needle) to exit opening 516 at a predetermined angle and/or controlled distance from the face of phased array sensor 508*a*. In many embodiments, the phased array sensor 508*a* may include at least 2 adjacent elements (e.g., ultrasound imaging elements). In several embodiment the number of adjacent elements in the phased array sensor 508*a* may be adjusted to optimize the length of the transducer subassembly 536 with target image size. For example, reducing the number of elements in the phased array shortens the length of the transducer subassembly, but it also narrows the image. In some instances, different embodiments may include different numbers of adjacent elements, enabling an operator to choose based on personal preference. In various embodiments, the phased array sensor 508*a* may include elements on the proximal and distal sides of opening 516. In some such embodiments, a controller (e.g., controller 610) may be utilized to cause the physically separated elements to act as a single continuous array that provides an image including areas distal and proximal to opening 516.

In some embodiments, the phased array sensor 508*a* may be mounted to a rotatable collar. In some such embodiments, the phased array sensor 508*a* may be utilized to produce a 360-degree radial image. In various embodiments, the rotatable collar may include a plurality of conductive rings to maintain a conductive and/or communicative coupling between the phased array sensor 508*a* and a controller (e.g., controller 110). In some embodiments, a fluid reservoir and/or delivery port, such as an expandable balloon may be included in or around the transducer subassembly 536. In some such embodiments, fluid may be introduced into the fluid reservoir, or the body lumen, via the fluid delivery port to improve coupling between the phased array sensor 508*a* and the body lumen. In various embodiments, the fluid coupling may be used in larger diameter body lumens where the transducer subassembly 536 is not wedged against the wall of the body lumen.

In various embodiments, one or more of articulation joints 504*a*, 504*b*, 504*c* may enable dual mode steerability. Dual mode steerability may allow for bi-directional steering of the distal steering assembly 538 plus separate steerability of the transducer subassembly 536 independent of the rest of the distal steering assembly 538 (including opening 516 between articulation joints 504*a*, 504*b*). Steering wires 526*a*, 526*b*, may be utilized to actuate articulation joint 504*b*. The pull wire 528 may be utilized to deflect the transducer subassembly 536 independent of the rest of the distal steering assembly 538. More generally, pull wire 528 may comprise a deflection wire. In many embodiments, a handle may be attached to the proximal end 510 of elongate member 502. In many such embodiments, the handle may include one or more control features that allow an operator to adjust the articulations joints. Several embodiments may include a steering mechanism that can include locking and/or tensioning control features. In some embodiments, the locking and/or tensioning control features may enable the transducer subassembly 536 to stay in place without an operator needing to keep a finger on the steering mechanism. In one embodiment, deflection of the transducer subassembly 536 may be controlled by a push mechanism (as opposed to a pull or tension mechanism).

Referring to FIG. 5B, a transverse cross-sectional view looking toward the distal end 512 of elongate member 502 at cutting plane 540 is shown. The suction channel 530 may terminate at the distal end of elongate member 502. In various embodiments, the suction channel 530 may be used to clear mucus from the face of the optical imaging sensor 508*b*. In some embodiments, the suction channel 530 may have a diameter between 0.7 and 1 mm, such as 0.889 mm.

Referring to FIG. 5C, deflection of the transducer subassembly 536 may be limited by hard stops 524. In some embodiments, actuation members 532*a*, 532*b* may comprise rods for articulation of the transducer subassembly 536. In one or more embodiments, actuation members 532*a*, 532*b* may comprise stainless steel. In a variety of embodiments, in the absence of external input, the transducer subassembly 536 may align with the rest of the distal steering assembly 538. For example, a series of wires may be attached (e.g., welded) between the transducer subassembly 536 and the rest of the distal steering assembly 538. In such examples, the transducer subassembly 536 may return to a nominal straight position when tension of the pull wire 528 is released. In one embodiment, the series of wires may be replaced by a pin and spring (e.g., torsion, tension, or compression spring) that facilitates a return to the nominal straight position when the external force (e.g., pushing/pulling force) is removed from the deflection wire. In various embodiments, one or more of the wires (e.g., pull wire 528, steering wires 526*a*, 526*b*) may be covered with a braid and reflowed polymer to prevent pinch points or foreign object ingress (e.g., Bowden cable). Several embodiments may utilize a braid with a low number of wires (low pick count) and/or loosely packed (not dense). The braid may provide a scaffolding to reflow a polymer into to create a smooth outer surface without impacting flexibility and/or deflection while preventing pinch points.

Figure 6:
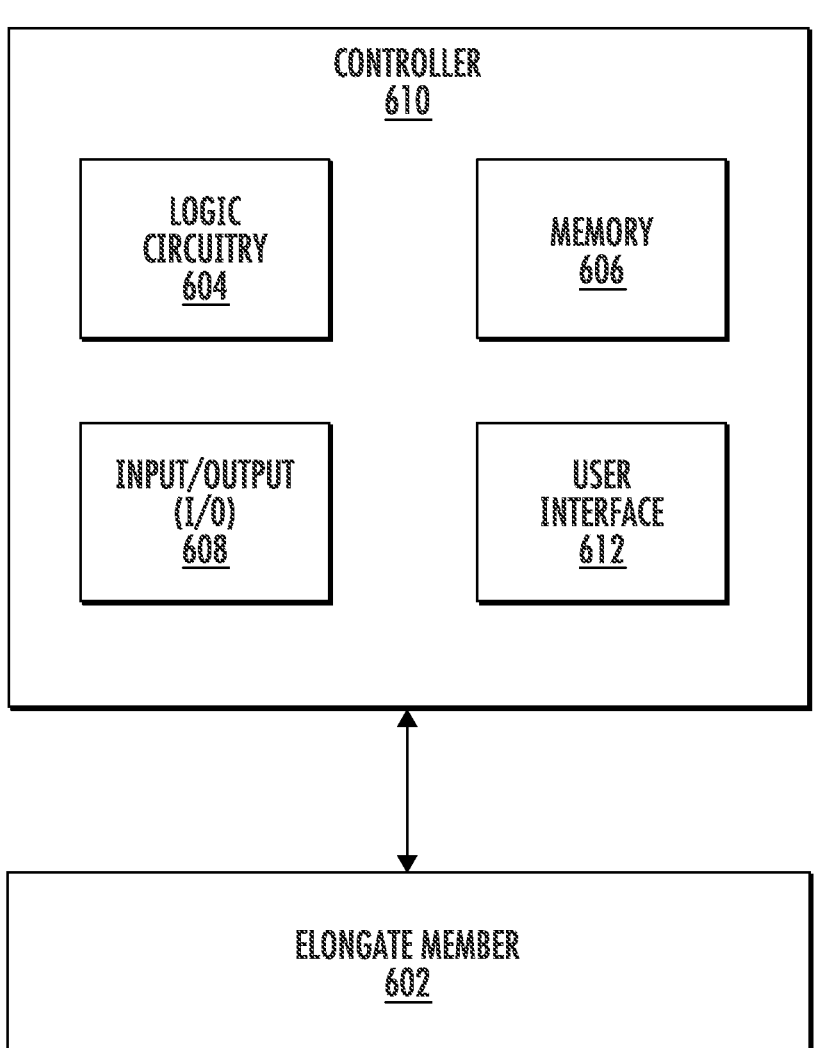
FIG. 6 illustrates various aspects of an exemplary controller of a medical device according to one or more embodiments disclosed hereby.

FIG. 6 illustrates various aspects of a controller 610 of a medical device 600 according to one or more embodiments disclosed hereby. In the illustrated embodiment, the medical device 600 includes controller 610 and elongate member 602. Controller 610 includes logic circuitry 604, memory 606, input/output (I/O) 608, and user interface 612. In various embodiments, controller 610 may enable interaction with and control over components of elongate member 602. For example, controller 610 may generate and present images based on signals received from a transducer in response to signals sent to the transducer by controller 610. In some embodiments, FIG. 6 may include one or more components that are the same or similar to one or more other components of the present disclosure. For example, elongate member 602 may be the same or similar to elongate member 502. Further, one or more components of FIG. 6, or aspects thereof, may be incorporated into other embodiments of the present disclosure, or excluded from the described embodiments, without departing from the scope of this disclosure. For example, controller 610 may be utilized in conjunction with elongate member 202 without departing from the scope of this disclosure. Still further, one or more components of other embodiments of the present disclosure, or aspects thereof, may be incorporated into one or more components of FIG. 6, without departing from the scope of this disclosure. For example, transducers 108 may be incorporated into elongate member 602 without departing from the scope of this disclosure. Embodiments are not limited in this context.

In various embodiments, controller 610 may implement one or more functionalities disclosed hereby. For example, instructions stored in member 606 may be executed by logic circuitry 604 to operate phased array sensor 508a and generate images on user interface 612 based on signals received from the phased array sensor 508a. In many embodiments, controller 610 may automate one or more functions. Logic circuitry 604 may send and receive signals from transducers in elongate member 602 via I/O 608. In many embodiments, logic circuitry 604 may generate metadata for signals received from transducers. In many such embodiments, the metadata may correspond to signals from one or more other transducers in elongate member 602. For example, positions of the elongate member 602 indicated by an EM tracking sensor may be associated with images from a phased array of ultrasound imaging elements as metadata.

In several embodiments, logic circuitry 604 may perform image processing. For example, stitch a plurality of images generated by transducer 406a together to create a composite image of the interior of a body. In some embodiments, logic circuitry 604 may utilize data from multiple transducers to perform mapping, such as by generating composite images. For example, position data (e.g., in 6 DOF) may be combined with images to generate composite images. In some embodiments, metadata associated with an image may indicate the position (e.g., in 6 DOF) of the imaging sensor when the imaging sensor captured the image. In various embodiments, a plurality of images may be combined to generate a radial image. In various such embodiments, a plurality of radial images may be combined to generate a composite image of an interior portion of a body.

In one or more embodiments, data from pre-operative scans may be stored in memory 606 and/or utilized by logic circuitry 604. In some embodiments, logic circuitry 602 may utilize the pre-operative data in conjunction with operative data (e.g., sensor data received from elongate member 602) to determine the position of elongate member 602. For example, logic circuitry 604 may match landmarks identified in pre-operative images to elements in images generated via elongate member 602 to determine the position of the elongate member 602.

In some embodiments, logic circuitry 602 may perform motion compensation. For example, logic circuitry 602 may compensate for respiratory motion. In various embodiments, motion compensation may facilitate matching operative data with pre-operative data (e.g., from a computed tomography (CT) scan). For example, motion compensation may enable operative images to be overlayed on pre-operative images.

In various embodiments, logic circuitry 602 may perform one or more of object detection, distance estimation, and object classification. In various such embodiments, logic circuitry 602 may identify a mass from a plurality of ultrasound images, determine a distance to the mass based on the plurality of ultrasound images, and classify the mass based on the size, position, and distance of the mass. In several embodiments, logic circuitry 602 may utilize data from pre-operative scans to classify the mass, such as by matching the mass to a landmark identified in a pre-operative image. For example, a target nodule for biopsy located in a peripheral portion of a lung may be confirmed by comparing an object detected in an ultrasound image to one or more pre-operative images comprising the target nodule. In many embodiments, object detection and classification may be used for boundary detection, such as for identifying airway branches.

In many embodiments, logic circuitry 602 may generate a three-dimensional model of one or more portions of the interior of a body. In some embodiments, one or more techniques described hereby may be utilized to generate the three-dimensional model, such as transducer data, pre-operative data, composite images, metadata, images, positions, objects, distances, object classifications, and the like. In various embodiments, the three-dimensional model may include the position of the elongate member 602.

In various embodiments, an operator may cause logic circuitry 604 to carry out various functions by providing input via user interface 612. In some embodiments, image generation may be controlled via user interface 612. In one or more embodiments, object classifications may be controlled via user interface 612. For example, a user may add or remove classifications by selecting objects in an image presented via the user interface 612. In several embodiments, logic circuitry may determine a distance between two points identified in an image presented via the user interface 612. For example, logic circuitry 602 may determine a distance between two objects selected by a user in an image. In many embodiments, output may be presented to an operator via user interface 612. For example, a three-dimensional model of a portion of the interior of a body may be presented via user interface 612.

In many embodiments, additional and/or updated functionality may be integrated into controller 610, such as by storing additional and/or updated instructions on memory 606 (e.g., as software). In one or more embodiments, controller 610 may be connected to a network (e.g., the internet, a local area network, a personal area network, or inductive coupling). In one or more such embodiments, controller 610 may be updated and/or provided with additional functionality by receiving instructions over the network.

In several embodiments, controller 610 may automate one or more functionalities. In many embodiments, controller 610 may automate functionalities by using a feedback loop-based data from one or more of transducers to control one or more of the same or other transducers. For example, data from position sensors may be utilized to control one or more actuators disposed in actuation joints. In such examples, the feedback loop may be used in automating navigation and/or positioning of the elongate member 602 to a target site. In some embodiments, elongate member 602 may have wires for controlling articulation joints that extend to the proximal end. In some such embodiments, servo motors coupled to the wires and operable by controller 610 may enable automated steering of the elongate member using data from one or more transducers (e.g., 208*b* and/or 208*c*). In one embodiment, electromagnetic position sensors may be disposed along the length of the elongate member, such as at articulation joints.

In various embodiments, a CT scans and mapping may be used to determine the approximate location of a target site (e.g., target lesion) and a virtual map of corresponding portions of a body (e.g., lungs). In various such embodiments, controller 610 may utilize the CT scans and/or mapping in conjunction with data from transducers to automate navigation to a target site. In one or more embodiments, biopsy acquisition may be at least partially automated. For example, imaging data (e.g., from 208*a*) may be utilized by controller 610 in conjunction with a needle actuator to acquire a biopsy of target tissue. In various embodiments, controller 610 may utilize an aspirator to automate biopsy acquisition. In some embodiments, the controller 610 may acquire samples from a variety of places at the target site (e.g., via feathering). In many embodiments, controller 610 may track and record locations for each biopsy. In many such embodiments, data from the locations of biopsies may be utilized to determine characteristics of a target site, such as the size and boundaries of a lesion. In several embodiments, various automated function may be controlled, or directed, via user interface 612. For example, target locations for biopsies may be identified via a touch screen based on real-time images from one or more imaging transducers. In another examples, a direction to take in a branching lumen may be identified based on user input.

Figure 7:
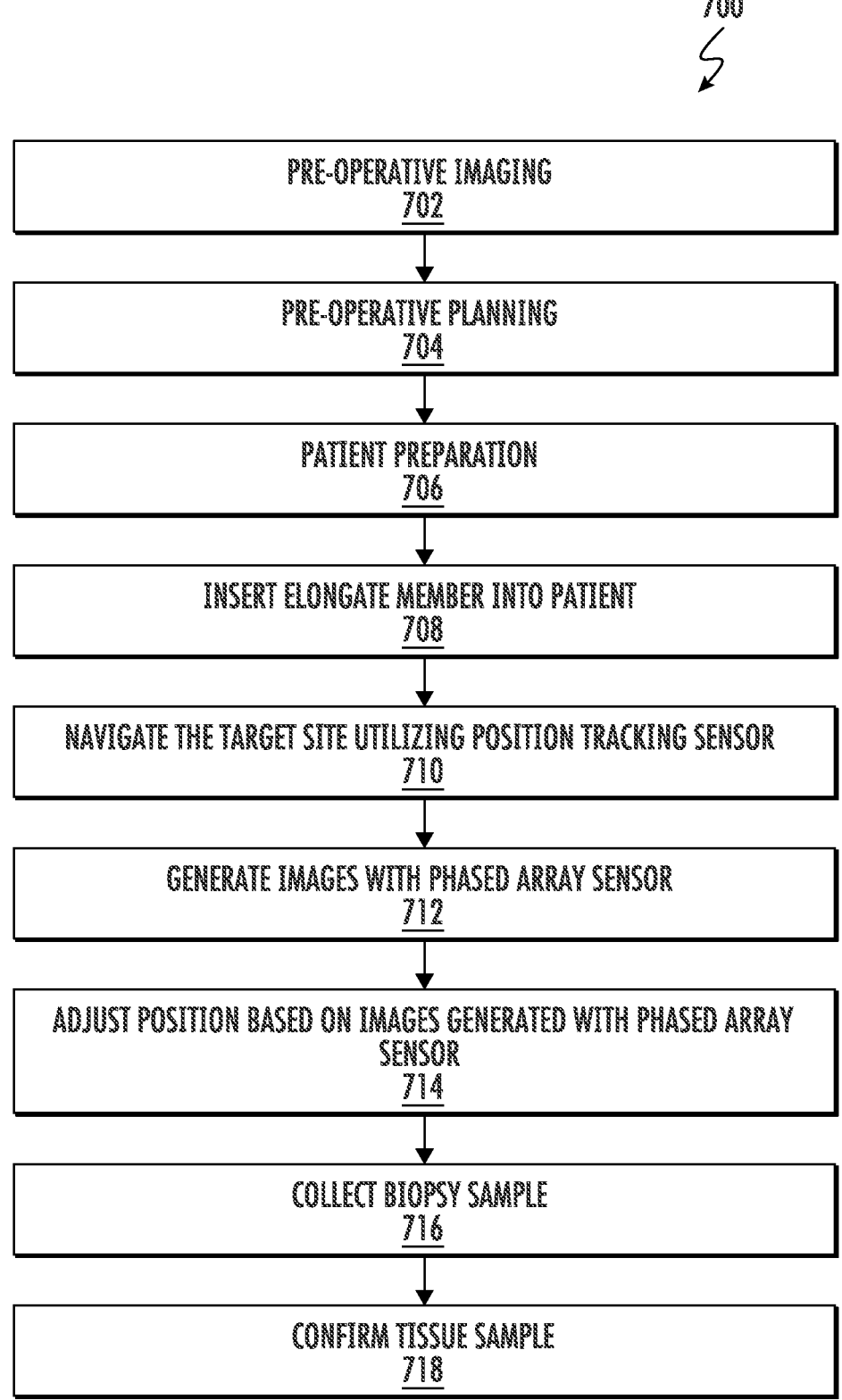
FIG. 7 illustrates an exemplary process flow according to one or more embodiments disclosed hereby.

FIG. 7 illustrates a process flow 700 according to one or more embodiments disclosed hereby. In various embodiments, one or more portions of process flow 700 may be implemented by or with components disclosed hereby. For example, blocks 708 through 718 may be implemented with medical device 100 or medical device 600. Embodiments are not limited in this context.

In the illustrated embodiment, process flow 700 may begin at block 702. At block 702 "pre-operative imaging" pre-operative imaging may be performed. For example, pre-operative imaging may be performed to determine the position of a target site (e.g., potentially cancerous nodule) within a peripheral airway. The pre-operative imaging may utilize one or more external imaging techniques, such as one or more of X-rays (e.g., as part of CT scans), magnetic resonance imaging (MRI), and ultrasound imaging. Continuing to block 704 "pre-operative planning" pre-operative planning may be performed. For example, a procedural plan (e.g., a route) for acquiring a biopsy of the target site may be developed. In some embodiments, pre-operative planning may include providing one or more of the pre-operative images to controller 110 or controller 610.

Proceeding to block 706 "patient preparation" patient preparation may be performed. For example, a patient may be sedated and positioned to receive the elongate member. In many embodiments, the patient may be positioned based on their position during pre-operative imaging. At block 708

"insert the elongate member" the elongate member may be inserted into the patient. For example, the distal end of elongate member 102 may be inserted into a patient, such as via the nose or mouth. Continuing to block 710 "navigate to target site utilizing position tracking sensor" a position tracking sensor may be utilized to navigate the distal end of an elongate member to the target site. For example, position tracking sensor 508*c* comprising a TMR sensor may be used to navigate to the target site. In various embodiments, the position tracking sensor 508*c* may include a TMR 6-DOF sensor. In some embodiments, controller 110 or controller 610 may utilize pre-operative images in conjunction with feedback from one or more position tracking sensors (e.g., position tracking sensor 508*c*) to provide guidance for navigating the target site. In several embodiments, articulation joints (e.g., articulation joints 504*a*, 504*b*, 504*c*) may be utilized to maneuver the elongate member and enable navigation to the target site based on the position tracking sensor.

At block 712 "generate images with phased array sensor" images may be generated with a phased array sensor. For example, controller 610 may generate images based on feedback from the phased array sensor 508*a*. Continuing to block 714 "adjust position based on images generated with phased array sensor" the position of the elongate member may be adjusted based on images generated with the phased array sensor. For example, positioning of the elongate member may be fine-tuned to finally position the elongate member for actuation of a biopsy needle inserted through a lumen of the elongate member. Proceeding to block 716 "collect biopsy sample" a biopsy sample may be collected. For example, biopsy needle 520 may be extended from opening 516 in the outer surface 514 of elongate member 502 to acquire a tissue sample. At block 718 "confirm tissue sample" the tissue sample may be confirmed. For example, the biopsy needle 520 may be removed from lumen 506*a* for visually confirming the tissue sample was acquired.

In some embodiments, the tissue sample(s) collected and sent to a pathology lab for diagnosis. In various embodiments, rapid on-site evaluation (ROSE) may be performed, such as with a pathologist being present to analyze the tissue sample and determine a diagnosis. In various such embodiments, real-time confirmation may enable the biopsy needle to be replaced with a therapeutic probe that can be used to treat the target site. The therapeutic probe may include or utilize one or more of radio frequency (RF) waves, microwaves, cryogenic, fluids, irreversible electroporation (IRE), or other ablation modalities. In some embodiments, the therapeutic probe may be used to deliver therapeutic agents, such as chemo spheres, to the target site.

Figure 8:
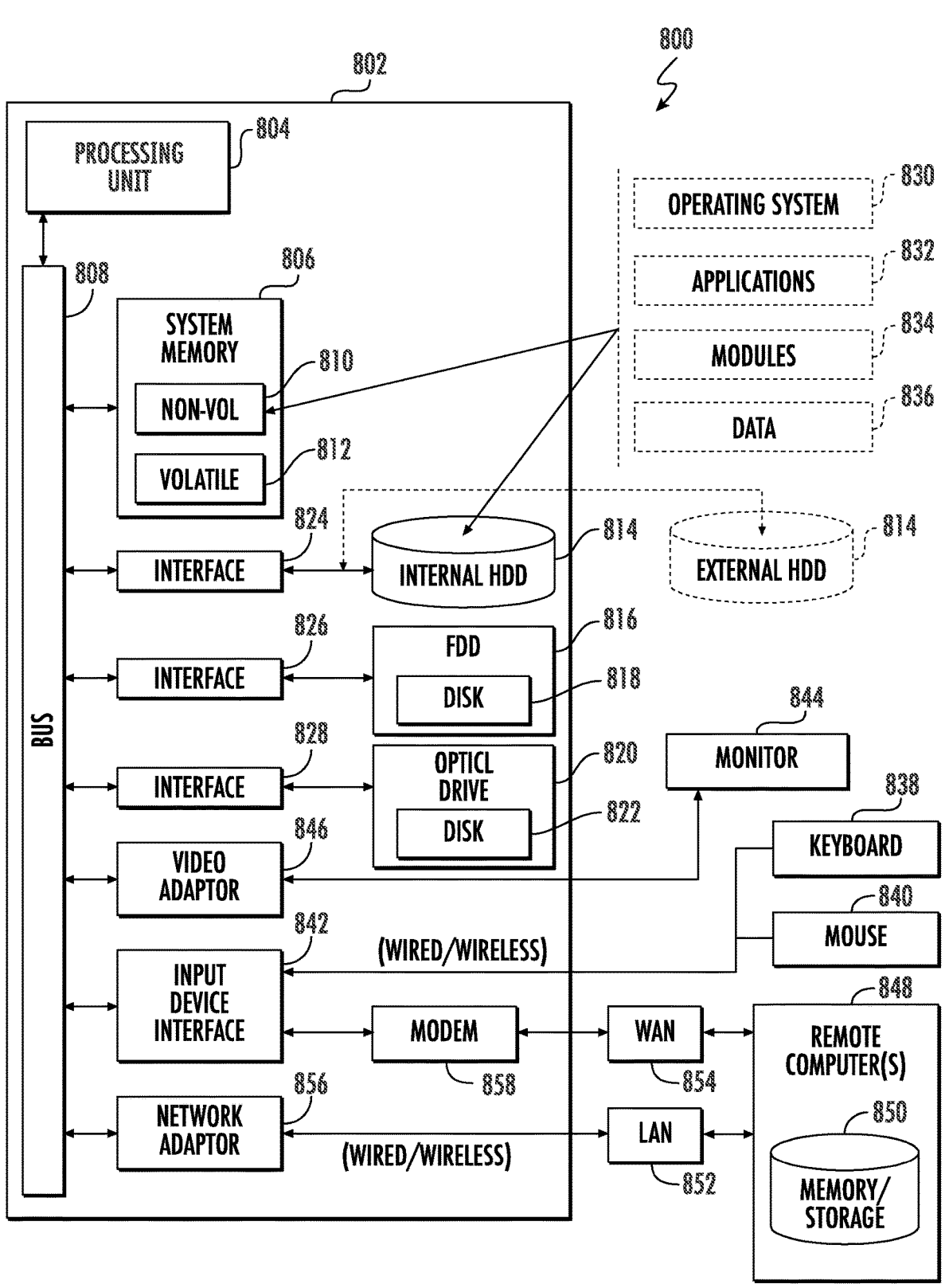
FIG. 8 illustrates an exemplary computing architecture according to one or more embodiments disclosed hereby.

FIG. 8 illustrates a computing architecture 800 according to one or more embodiments disclosed hereby. The computing architecture 800 may be suitable for implementing various embodiments as previously described. In various embodiments, the computing architecture 800 may comprise or be implemented as part of an electronic device and/or medical device. In some embodiments, the computing architecture 800 may be representative, for example, of one or more components described hereby. In some embodiments, computing architecture 800 may be representative, for example, of a computing device that implements or utilizes one or more portions of components and/or techniques described hereby, such as controller 110, transducers 108, controller 610, logic circuitry 604, memory 606, I/O 608, and/or user interface 612. The embodiments are not limited in this context.

As used in various embodiments herein, the terms "system" and "component" and "module" can refer to a computer-related entity, either hardware, a combination of hardware and software, software, or software in execution, examples of which are provided by the exemplary computing architecture 800. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a controller 110 and the controller 110 can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 800 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 800.

As shown in FIG. 8, the computing architecture 800 comprises a processing unit 804, a system memory 806 and a system bus 808. The processing unit 804 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 804.

The system bus 808 provides an interface for system components including, but not limited to, the system memory 806 to the processing unit 804. The system bus 808 can be any of several types of bus structure that may further interconnect to a memory bus (with or without a memory controller), a peripheral bus, and a local bus using any of a variety of commercially available bus architectures. Interface adapters may connect to the system bus 808 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 806 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory (e.g., one or more flash arrays), polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 8, the system memory 806 can include non-volatile memory 810 and/or volatile memory 812. In some embodiments, system memory 806 may include main memory. A basic input/output system (BIOS) can be stored in the non-volatile memory 810.

The computer 802 may include various types of computer-readable storage media in the form of one or more lower speed memory units, including an internal (or external) hard disk drive (HDD) 814, a magnetic floppy disk drive (FDD) 816 to read from or write to a removable magnetic disk 818, and an optical disk drive 820 to read from or write to a removable optical disk 822 (e.g., a CD-ROM or DVD). The HDD 814, FDD 816 and optical disk drive 820 can be connected to the system bus 808 by an HDD interface 824, an FDD interface 826 and an optical drive interface 828, respectively. The HDD interface 824 for external drive implementations can include at least one or both of Universal Serial Bus (USB) and Institute of Electrical and Electronics Engineers (IEEE) 994 interface technologies. In various embodiments, these types of memory may not be included in main memory or system memory.

The drives and associated computer-readable media provide volatile and/or nonvolatile storage of data, data structures, computer-executable instructions, and so forth. For example, a number of program modules can be stored in the drives and memory units 810, 812, including an operating system 830, one or more application programs 832, other program modules 834, and program data 836. In one embodiment, the one or more application programs 832, other program modules 834, and program data 836 can include or implement, for example, the various techniques, applications, and/or components described hereby.

A user can enter commands and information into the computer 802 through one or more wire/wireless input devices, for example, a keyboard 838 and a pointing device, such as a mouse 840. Other input devices may include transducers 108, phased array sensor 508$a$, optical imaging sensor 508$b$, position tracking sensor 508$c$, microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 804 through an input device interface 842 that is coupled to the system bus 808 but can be connected by other interfaces such as a parallel port, IEEE 994 serial port, a game port, a USB port, an IR interface, and so forth.

A monitor 844 or other type of display device is also connected to the system bus 808 via an interface, such as a video adaptor 846. The monitor 844 may be internal or external to the computer 802. In addition to the monitor 844, a computer typically includes other peripheral output devices, such as speakers, printers, and so forth.

The computer 802 may operate in a networked environment using logical connections via wire and/or wireless communications to one or more remote computers, such as a remote computer 848. In various embodiments, one or more interactions described hereby may occur via the networked environment. The remote computer 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wire/wireless connectivity to a local area network (LAN) 852 and/or larger networks, for example, a wide area network (WAN) 854. Such LAN and WAN networking environments are commonplace in offices and companies, and facilitate enterprise-wide computer networks, such as intranets, all of which may connect to a global communications network, for example, the Internet.

When used in a LAN networking environment, the computer 802 is connected to the LAN 852 through a wire and/or wireless communication network interface or adaptor 856. The adaptor 856 can facilitate wire and/or wireless communications to the LAN 852, which may also include a wireless access point disposed thereon for communicating with the wireless functionality of the adaptor 856.

When used in a WAN networking environment, the computer 802 can include a modem 858, or is connected to a communications server on the WAN 854 or has other means for establishing communications over the WAN 854, such as by way of the Internet. The modem 858, which can be internal or external and a wire and/or wireless device, connects to the system bus 808 via the input device interface 842. In a networked environment, program modules depicted relative to the computer 802, or portions thereof, can be stored in the remote memory/storage device 850. It will be appreciated that the network connections shown are exemplary and other means of establishing a communications link between the computers can be used.

The computer 802 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor (e.g., logic circuitry), which when read by a machine causes the machine to fabricate logic to perform the techniques described hereby. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine (e.g., logic circuitry), may cause the machine to perform a method and/or operation in accordance with the embodiments. Such a machine may include, for example, any suitable processing platform, computing platform, computing device, processing device, computing system, processing system, computer, processor, logic circuitry, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

All of the devices and/or methods disclosed and claimed hereby can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method disclosed hereby without departing from the concept, spirit and scope of the disclosure. All such similar substitutes and modifications apparent to those skilled in the art are deemed to be within the spirit, scope and concept of the disclosure as defined by the appended claims.

What is claimed is:

1. An apparatus, comprising:

an elongate member with dual mode steerability comprising an outer surface, a proximal end, a distal end, and at least two articulation joints disposed between the proximal end and the distal end;

a lumen having a first opening disposed between ones of the at least two articulation joints and a second opening proximate the distal end of the elongate member; and a transducer comprising a phased array sensor of at least two elements, disposed proximate the distal end of the elongate member, wherein the transducer is configured to be moved independently from the second opening, wherein a first portion of the phased array sensor is positioned distal to the second opening of the lumen and a second portion of the phased array sensor is positioned proximal to the second opening of the lumen.

2. The apparatus of claim 1, wherein a field of view of the transducer extends from the outer surface of the elongate member.

3. The apparatus of claim 1, wherein the second opening of the lumen is disposed in the outer surface of the elongate member.

4. The apparatus of claim 3, wherein the lumen includes a ramp configured to direct an instrument into a field of view of the transducer when the instrument extends through the lumen and out of the second opening of the lumen.

5. The apparatus of claim 4, wherein the ramp includes a multiple-radius bend.

6. The apparatus of claim 1, comprising a position tracking sensor.

7. The apparatus of claim 6, wherein the position tracking sensor comprises a magnetic tunnel junction.

8. The apparatus of claim 6, comprising an optical imaging sensor.

9. The apparatus of claim 1, comprising an optical imaging sensor.

10. The apparatus of claim 9, wherein a field of view for the transducer extends from the outer surface of the elongate member and a field of view for the optical imaging sensor extends from the distal end of the elongate member.

11. The apparatus of claim 9, wherein the optical imaging sensor is mounted on the distal end of the elongate member.

12. The apparatus of claim 1, the at least one articulation joint comprising a first articulation joint and a second articulation joint, wherein a direction of articulation of the first articulation joint is orthogonal to a direction of articulation of the second articulation joint.

13. The apparatus of claim 1, the at least one articulation joint comprising a first articulation joint and a second articulation joint, wherein the second opening of the lumen is disposed between the first and second articulation joints.

*   *   *   *   *